United States Patent
Maack et al.

(10) Patent No.: US 7,769,137 B2
(45) Date of Patent: Aug. 3, 2010

(54) PORTABLE X-RAY DETECTOR UNIT

(75) Inventors: Hanns-Ingo Maack, Norderstedt (DE); Waldermar Lumma, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 287 days.

(21) Appl. No.: 11/577,831

(22) PCT Filed: Oct. 25, 2005

(86) PCT No.: PCT/IB2005/053494

§ 371 (c)(1), (2), (4) Date: Apr. 24, 2007

(87) PCT Pub. No.: WO2006/046206

PCT Pub. Date: May 4, 2006

(65) Prior Publication Data

US 2009/0122960 A1   May 14, 2009

(30) Foreign Application Priority Data

Oct. 29, 2004   (EP)   .................................   04105393

(51) Int. Cl.
- *H05G 1/38* (2006.01)
- *H05G 1/08* (2006.01)
- *G01T 1/02* (2006.01)
- *G01T 1/24* (2006.01)
- *H01L 27/146* (2006.01)

(52) U.S. Cl. .................... 378/96; 378/98.8; 250/370.07; 250/370.09

(58) Field of Classification Search ................... 378/96, 378/98.8, 108, 111, 112, 114, 117, 189; 250/370.01, 250/370.07, 370.08, 370.09
See application file for complete search history.

(56) References Cited

U.S. PATENT DOCUMENTS

| | | | |
|---|---|---|---|
| 5,877,501 A * | 3/1999 | Ivan et al. ............... | 250/370.09 |
| 5,917,882 A * | 6/1999 | Khutoryansky et al. ..... | 378/116 |
| 6,047,042 A * | 4/2000 | Khutoryansky et al. ....... | 378/62 |
| 6,067,343 A | 5/2000 | Brendler et al. | |
| 6,151,383 A * | 11/2000 | Xue et al. ................... | 378/108 |
| 6,236,711 B1 | 5/2001 | Lumma | |
| 6,768,784 B1 | 7/2004 | Green et al. | |
| 7,359,482 B2 * | 4/2008 | Schmitt ..................... | 378/98.8 |
| 2001/0048734 A1 | 12/2001 | Uppaluri et al. | |
| 2004/0096035 A1 | 5/2004 | Yamazaki et al. | |
| 2004/0101100 A1 * | 5/2004 | Morii et al. ................. | 378/98.7 |
| 2004/0114725 A1 | 6/2004 | Yamamoto | |
| 2006/0071172 A1 * | 4/2006 | Ertel et al. ............. | 250/370.11 |
| 2007/0187610 A1 * | 8/2007 | Morii et al. ............ | 250/370.09 |

\* cited by examiner

*Primary Examiner*—Edward J Glick
*Assistant Examiner*—Anastasia Midkiff

(57) ABSTRACT

A portable X-ray detector unit includes a portable, hand-held cassette having exposure detection fields for measuring the level of radiation to which a subject to be imaged is exposed. An Automatic exposure control terminates radiation supplied to a subject when it is determined that the level of exposure exceeds a predetermined threshold as interpreted in the portable detector unit. A user-interface is provided to control the exposure detection fields and/or the automatic exposure control.

17 Claims, 4 Drawing Sheets

PORTABLE X-RAY DETECTOR UNIT

This invention relates generally to an X-ray imaging system and, more particularly to a portable x-ray detector unit for use in such a system.

It is widely known, in the field of non-invasive medical diagnosis to obtain a radiation image of a subject to be imaged by irradiating the object to be imaged with radiation and detecting the intensity distribution of the radiation that has been transmitted through the subject to be imaged.

Referring to FIG. 1 of the drawings, there is illustrated schematically a typical X-ray system, which comprises an ionisation chamber 1 arranged between an X-ray source 2 and an X-ray image detector 3 or between a patient 4 to be examined and the X-ray image detector 3. The ionisation chamber comprises a plurality of measuring fields in which the X-ray dose is measured and one (or more) of which can be selected for dose measurement.

The X-ray source 2 is fed by an X-ray generator which comprises a high voltage generator 5 and a control unit 6. During an X-ray exposure, ionisation currents are generated by the X-ray flow across the associated measuring field electrode in the previously selected measuring field of the ionisation chamber 1. These ionisation currents are integrated by the control unit 6 and ensure that the X-ray exposure is automatically terminated when a given integral value is reached, i.e. a given dose in the selected measuring field.

Portable X-ray systems are known which generally comprise a portable X-ray generating unit and a portable X-ray detector unit, for use in the case, for example, where a patient (typically in intensive care) is not well enough to be moved to the main X-ray station. The X-ray detector unit can be positioned in any desired orientation relative to the patient to be imaged. US Patent Application Publication No. US 2004/0114725 A1 describes a portable X-ray system comprising an adjustable X-ray tube and a portable detector unit including an ionisation chamber for performing automatic exposure control. A user interface is provided separately from the detector unit, and the detector unit is communicably coupled thereto via a cable and/or wireless connection.

By the very nature of the hand-held portable detector unit, it can be employed in landscape or portrait mode, and it can be used upside down or the right way up. In order to support automatic exposure control in all orientations, several (typically five) ionisation chambers may be required. However, in some orientations, only selected ionisation chambers may be usable for performing automatic exposure control, based on their positions relative to the patient in the required orientation. Thus, the operative needs to input information to the control system, via the user interface, identifying the ionisation chambers to be used for automatic exposure control.

In the system described in US Patent Application Publication No. US 2004 00114725 A, this is not particularly straightforward, because the automatic exposure control device and corresponding user interface is provided separately from the portable detector unit and, once the detector unit is in the required position and orientation relative to the patient, it is quite likely that the relative positions of the ionisation chambers will not be accurately visible from the position of the user interface, making it difficult for the operative to correctly identify the ionisation chambers to be used for automatic exposure control.

We have now devised an improved arrangement, and it is an object of the present invention to provide a portable X-ray detector unit which is easier and more convenient to use. It is also an object of the present invention to provide a portable X-ray system including such a detector unit.

Thus, in accordance with a first aspect of the present invention, there is provided a portable X-ray detector unit, said unit comprising an image detector for detecting the intensity distribution of X-rays that have been transmitted through a subject to be imaged, exposure detection means for detecting a level of radiation to which said subject is exposed and automatic exposure control means for controlling the level of radiation to which said subject is exposed.

The present invention extends to a portable X-ray system, comprising X-ray generating apparatus, and a portable detector unit as defined above.

Preferably, said hand-held unit further comprises a user interface for controlling operation of said automatic exposure control means, which enables the operative to enter the measuring fields to be used for automatic exposure control more easily and accurately than with prior art arrangements.

In fact, in accordance with a second aspect of the present invention, there is provided a portable X-ray detector unit, said unit comprising an image detector for detecting the intensity distribution of X-rays that have been transmitted through a subject to be imaged, exposure detection means for detecting a level of radiation to which said subject is exposed and for communicating a signal representative thereof to an automatic exposure control means for controlling the level of radiation to which said subject is exposed, said hand-held unit further comprising a user interface for controlling operation of said automatic exposure control means.

The automatic exposure control means may be removably connected to the image detector. The benefit of providing the detector unit as two separate components is that it can thereby be optimised for small dimensions and minimum weight. However, the automatic exposure control means may alternatively be integrated with said image detector, such that the total thickness of the image detector and the automatic exposure control means is less than it would be if they were provided in separate modules (no "double covers").

In fact, in accordance with a third aspect of the present invention, there is provided an automatic exposure control unit for use with a portable X-ray detector unit having an image detector for detecting the intensity distribution of X-rays that have been transmitted through a subject to be imaged, said automatic exposure control unit being arranged and configured to control the level of radiation to which said subject is exposed, and being removably connectable to said detector unit.

Also, in accordance with the third aspect of the invention, there is provided a portable X-ray detector unit for use with an automatic exposure control unit as defined above, and further comprising means for removably connecting said automatic exposure control unit thereto.

A connector may be provided on the detector unit or the automatic exposure control unit.

In a first exemplary embodiment, the detector unit is provided with a user interface for controlling operation of the automatic exposure control. This user interface may be provided in or on a handle provided on the detector unit. Alternatively, such a user interface may be provided on the automatic exposure control unit.

In a preferred embodiment, the detector may be arranged and configured to automatically switch from a detecting mode to a read-out mode when exposure of said subject to radiation has been terminated, for increased convenience and ease of use.

In one exemplary embodiment, the exposure detection means comprises a plurality of exposure measuring fields, and means are provided for user-selection of the exposure measuring fields to be used for automatic exposure control according to their proximity to said subject to be imaged. Thus, more convenient and accurate selection and input of the measuring fields is achieved. The automatic exposure control means is preferably arranged to cause exposure of said subject to radiation to be terminated once the level of exposure is determined to be sufficient relative to a predetermined threshold. The user interface may further comprise means for enabling a user to adjust the sensitivity of the detector and/or a predetermined exposure threshold. In one exemplary embodiment, the automatic exposure control means may be pre-programmed with default settings, which can be overridden by a user by adjustment via the user interface. Both of these features provide a flexibility not present in prior art arrangements.

Thus, the present invention provides a portable, hand-held X-ray detector unit in which the automatic exposure control device and/or the user interface for communicating therewith are integrated. So as to enable more convenient and accurate selection of the measuring fields to be used in the automatic exposure control according to their relative proximity to the subject to be imaged, which is dependent on the orientation of the detector, in use.

These and other aspects of the present invention will be apparent from, and elucidated with reference to, the embodiment described herein.

An embodiment of the present invention will now be described by way of example only and with reference to the accompanying drawings, in which.

Figure 1:
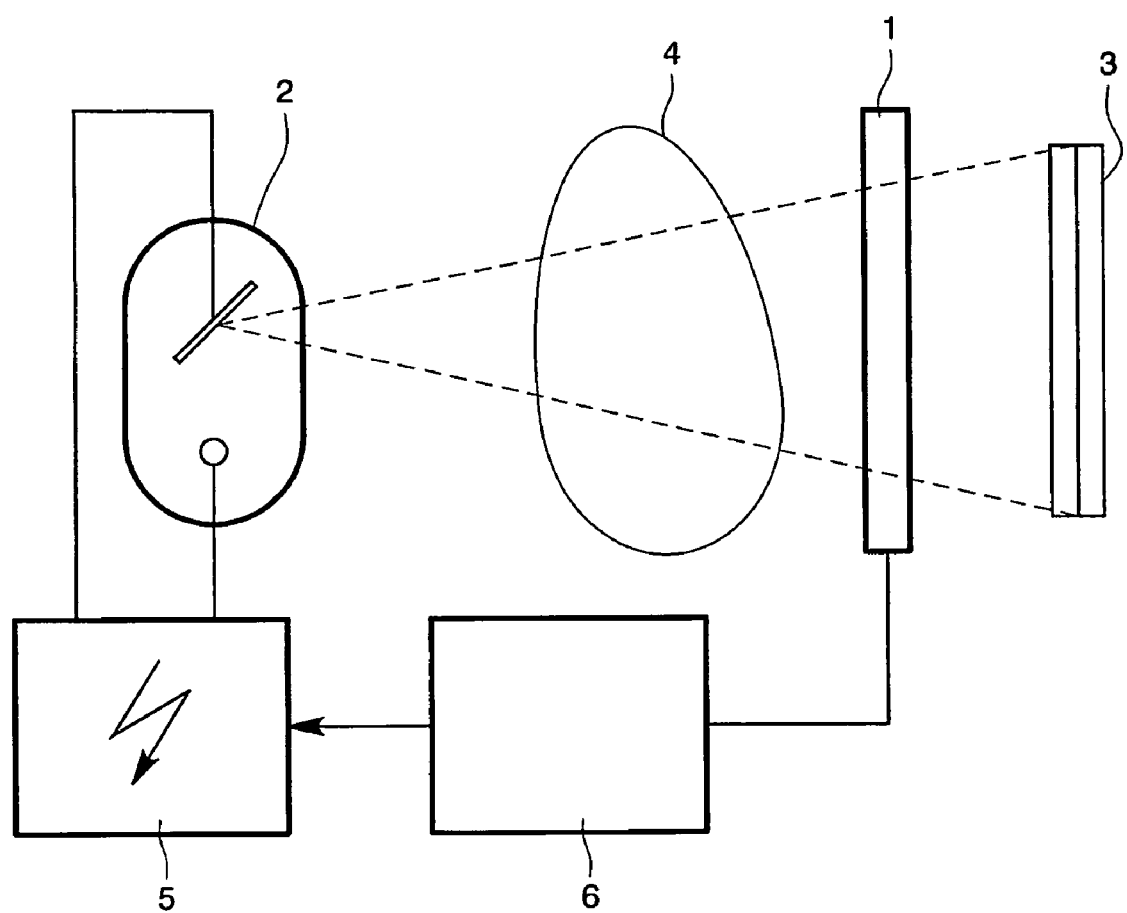
FIG. 1 is a schematic diagram illustrating the principal components of a typical X-ray system.
Figure 2:
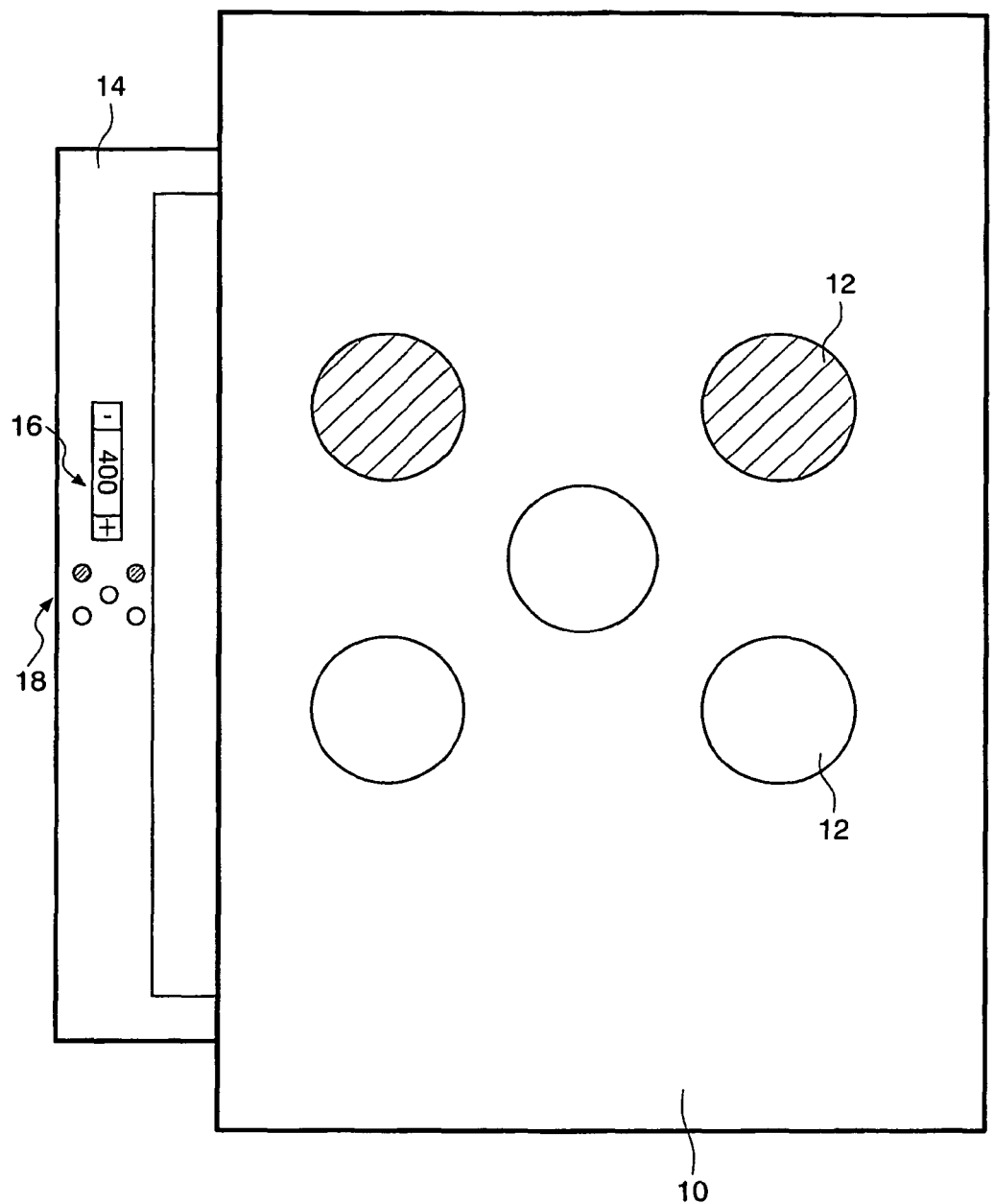
FIG. 2 is a schematic underside view of a portable X-ray detector unit according to an exemplary embodiment of the present invention.

Referring to FIG. 2 of the drawings, a portable, hand-held X-ray detector unit according to an exemplary embodiment of the present invention comprises a substantially rectangular cassette 10, within which is housed an image detector (not shown). The unit is provided with one or more ionisation chambers defining a plurality of exposure control measuring fields (denoted by the surface markings 12 on the cassette 10) for detecting, in use, a level of radiation to which a subject to be imaged is exposed.

U.S. Pat. No. 6,236,711 describes the construction of a suitable ionisation chamber for use in the detector unit of the present invention, which will now be described in more detail. However, it will be appreciated that the present invention is not intended to be limited with regard to the specific nature or construction of the exposure detection means.

Figure 3:
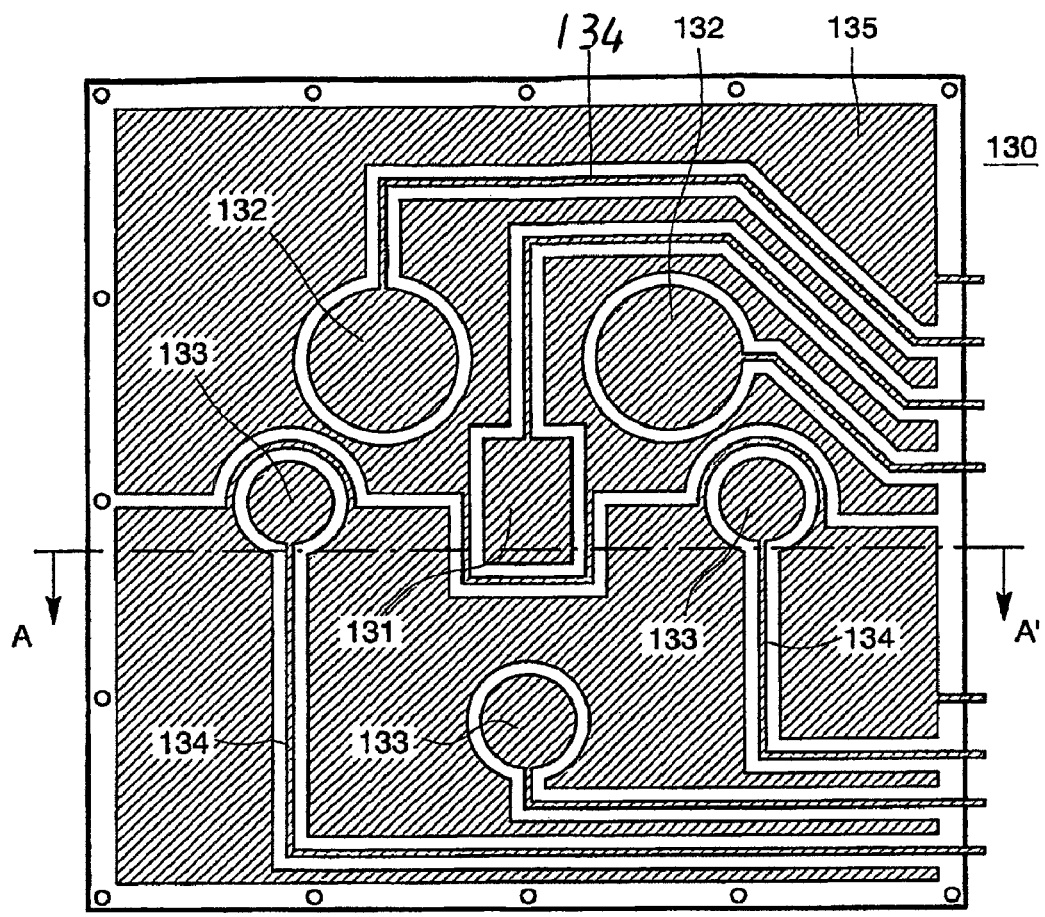
FIG. 3 is a plan view of the arrangement of measuring field electrodes on a substrate in an ionisation chamber for use in an exemplary embodiment of the present invention.
Figure 4:
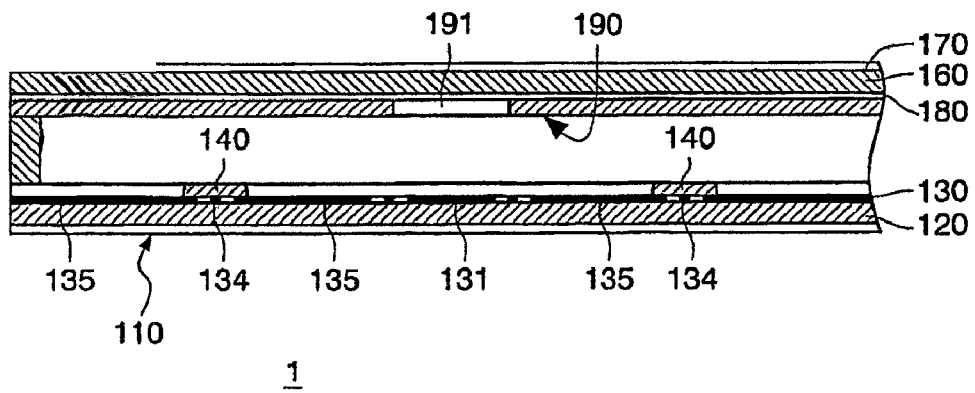
FIG. 4 is a schematic cross-sectional view of an ionisation chamber for use in an exemplary embodiment of the present invention.

Referring to FIGS. 3 and 4 of the drawings, the illustrated ionisation chamber consists of a flat housing with plane, square side walls, one of which supports the measuring field electrodes whereas the other supports the large-area electrode which carries a negative potential with respect to the measuring field electrodes in the operating condition, so that the electrons released in the electrode by the X-rays can reach the measuring field electrodes.

As appears from FIG. 4, the lower wall of the ionisation chamber housing comprises a substrate 120 of an insulating material, for example, a plexiglass plate. The outer side of the substrate 120 is provided with a thin, conductive layer 110 which electrically insulates the ionisation chamber from the environment.

The measuring field electrodes are provided in a layer 130 on the inner side of the substrate 120. As shown, in one exemplary embodiment, there is provided a central measuring field with a measuring field electrode 131, two measuring fields which are situated above the horizontal central line, symmetrically with respect to the vertical central line which comprise measuring field electrodes 132, and three smaller measuring fields which are 90° offset relative to one another about the centre and each of which comprises a measuring electrode 133. Each measuring electrode is connected, via a supply lead 134 provided on the substrate, to a respective integrator circuit which is provided in an automatic exposure control unit and has a high-ohmic input so as to integrate the ionisation currents flowing to the measuring field electrodes.

At the area of the supply leads 134, the layer 130 is provided with an insulating layer 140 which covers the supply leads and the intermediate spaces to the grounded drain electrode 135.

The second chamber wall comprises a substrate 160 of the same material and the same thickness as the substrate 120. The outer side of the substrate is provided with a conductive layer 170 which has the same function as the layer 110. On the inner side of the substrate there is formed a locally uniform, electrically conductive layer 180, which should be sufficient to generate an adequate number of free electrons under the influence of X-rays, but should be thin enough to cause only slight overall attenuation of the X-rays.

On the electrode layer 180, there is provided an insulating layer 190 which is provided with openings 191 in the region facing the measuring field electrodes, the charge carriers generated in the electrode in this region can emerge through the openings and reach, after charge carrier multiplication in the intermediate air space, the oppositely situated measuring field electrode.

The insulating layers 190, 140 effectively ensure that charge carriers are not emitted by the electrode 180 at the area of the supply leads or that they cannot strike or be incident on the supply leads 134. The X-ray transparency of these insulating layers is so high that reproduction of the pattern formed by the layers in the X-ray image is practically precluded.

Referring back to FIG. 2 of the drawings, and as stated above, one or more ionisation chambers are housed in the cassette 10 of the portable detector unit according to this exemplary embodiment of the present invention. Each ionisation chamber comprises one or more top, and corresponding bottom electrodes with air in between them to absorb X-rays. A DC voltage (around 300-500 V) is connected to the electrodes, and a DC/DC converter (not shown) is provided to generate this voltage. Markings 12, indicating to the operative the positions of the exposure control measuring fields, are provided on the outer face of the cassette 10.

The detector unit further comprises a handle 14 coupled to the cassette 10 and, housed within the handle 14, a programmable automatic exposure control unit including a comparator with programmable threshold voltage for switching off the incident radiation when a predetermined exposure level has been reached. A user interface, comprising sensitivity display and adjustment buttons 16 and field selection display and on/off buttons 18, is provided on the handle. In use, the operator positions the unit as required relative to the subject to be imaged, and then determines from the markings 12, which exposure control measuring fields should be selected (due to their relative proximity to the subject to be imaged). These fields can then be selected using the field selection buttons 18, such that only the selected measuring fields will be operative.

Figure 5:
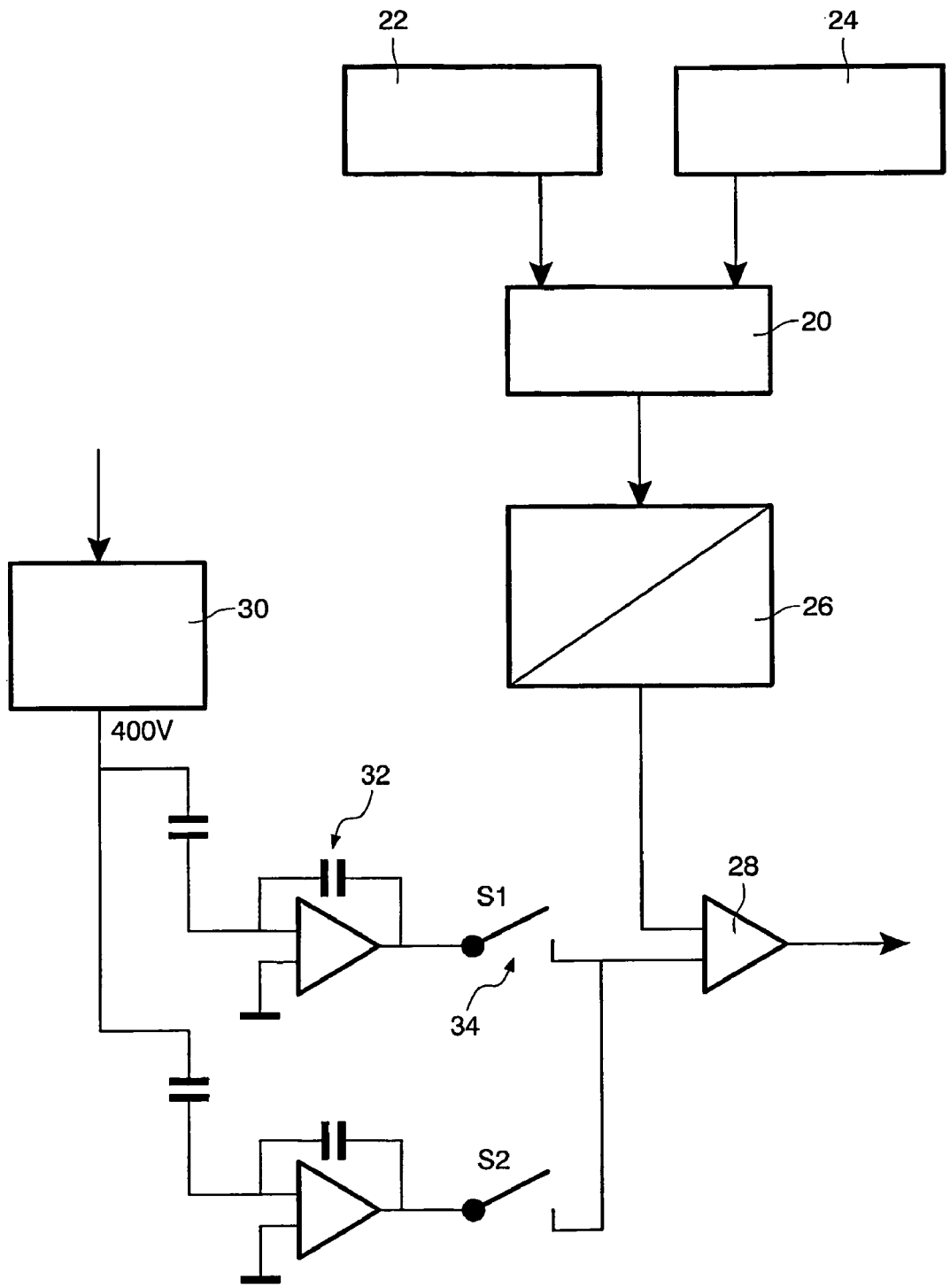
FIG. 5 is a schematic block diagram illustrating the principal components of an automatic exposure control device for use in a detector unit according to an exemplary embodiment of the present invention.

Referring to FIG. 5 of the drawings, the programmable automatic exposure control unit comprises a processor 20 which receives data indicative of pre-programmed settings 22 for the exposure system (which may, for example, be default settings) and/or user interface field selections (set using the field selection display buttons 18) and dose settings 24 (set using sensitivity display and adjustment buttons 16), which settings may override the default settings. It will be appreciated that many different user-programmable functions may be provided and controlled via the user interface. The processor 20 is connected to a digital-to-analogue converter 26 to create an exposure control voltage which is fed to a first input of a comparator 28.

A DC/DC converter 30 is provided for generating the DC voltage connected to the electrodes of the ionisation chambers 32. Each chamber 32 is connected to the second input of the comparator 28 via a respective switch 34 (S1, S2). The field selection performed by the user, and entered via the user interface, will determine which switches 34 (S1, S2) are closed, i.e. the switches of the selected measuring fields will be closed and the rest will be open so that the respective chambers will not be used in the automatic exposure control process.

The exposure control voltage fed to the first input of the comparator 28 sets the threshold for the exposure control. When the value at the second input of the comparator 28 (from the active ionisation chambers 32) exceeds the predetermined threshold set by the exposure control voltage, the comparator 28 generates a signal which causes the X-ray supply to be terminated. The detector may be arranged and configured to then turn directly, and automatically, to read-out mode.

It will be appreciated that the total thickness of the detector with integrated exposure control can be thinner than the sum of a prior art detector and separate exposure control device (because both are housed within a single cover, rather than the two covers which would otherwise be required). This also results in lower X-ray absorption and higher image quality.

In another exemplary embodiment of the invention, the detector unit may be split into two separate components: the wage detector itself and the automatic exposure control (AEC) means which is removably connectable to the image detector. The AEC could also be integrated into a unit together with an anti-scatter grid. Effectively, the key idea remains the same as that underlying the first exemplary embodiment described above, ie, the exposure control means is controlled as part of the detector unit, and requires no separate connection to the X-ray generator. This can be achieved, for example, by means of a connector between the exposure control means and the image detector unit when they are connected together. In this case, the image detector handle would be an ideal location for the user interface for controlling the exposure control means (AEC). Alternatively, the detector handle could be designed to form a combined 'subsystem handle' with a handle provided on a separate integrated AEC/grid device, which subsystem handle would carry the user interface. Either way, some of the main issues which may need to be considered in designing the (possibly 'clip-on') connector for mounting the AEC and image detector together, are to provide a power supply to the AEC, provide a logical interface to the AEC as input (target speed, KV etc) and provide and X-Ray synchronising signal or an output. By splitting the AEC from the detector, the detector can be optimised for small dimensions and minimum weight. The AEC portion can be integrated into a subsystem together with an anti-scatter grid, which will be known in the art and is provided as standard for many applications.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A detector unit comprising:
    an image detector for detecting an intensity distribution of X-rays that have been transmitted through a subject to be imaged;
    an exposure detector for detecting a level of radiation to which said subject is exposed and for communicating a signal representative thereof to an automatic exposure controller for controlling a level of radiation to which said subject is exposed; and
    a user interface for controlling operation of said automatic exposure controller, wherein the user interface is provided on the image detector.

2. The detector unit according to claim 1, wherein said automatic exposure controller is integrated with said image detector.

3. The detector unit according to claim 1, wherein said exposure detector comprises exposure measuring fields, and the user interface enables user-selection of the exposure measuring fields to be used for automatic exposure control according to proximity of the exposure measuring fields to said subject to be imaged.

4. The detector unit according to claim 1, wherein said automatic exposure controller is configured to cause exposure of said subject to radiation to be terminated once the level of exposure is determined to be sufficient relative to a predetermined threshold.

5. The detector unit according to claim 1, wherein the user interface enables a user to adjust at least one of the sensitivity of the detector unit and a predetermined exposure threshold.

6. The detector unit according to claim 1, wherein the automatic exposure controller is pre-programmed with default settings, which can be overridden by a user by adjustment via the user interface.

7. A portable X-ray system, comprising an X-ray generating apparatus and the portable X-ray detector unit according to claim 1.

8. The detector unit according to claim 1, wherein the automatic exposure controller is removably connected to the image detector.

9. The detector unit of claim 1, further comprising markings on an outer face of the detector unit, wherein proximity of exposure measuring fields to the subject to be imaged is determined by the markings, the exposure measuring fields being used for automatic exposure control.

10. The detector unit according to claim 1, wherein the detector unit is portable.

11. The detector unit according to claim 1, wherein the user interface is provided on a handle of the detector unit.

12. The detector unit according to claim 1, wherein the automatic exposure controller is provided on a handle of the detector unit.

13. The detector unit according to claim 1, wherein both the user interface and the automatic exposure controller are provided on a handle of the detector unit.

14. The detector unit according to claim 1, wherein the user interface is integrated into the detector unit.

15. The detector unit according to claim 1, wherein the user interface is integrated into a handle of the detector unit.

16. The detector unit according to claim 1, wherein the user interface is removably connected to the detector unit.

17. The detector unit according to claim 1, wherein the exposure detector is integrated with the detector unit.

* * * * *